United States Patent [19]
Dessau et al.

[11] Patent Number: 5,147,837
[45] Date of Patent: Sep. 15, 1992

[54] TITANIA CONTAINING DEHYDROGENATION CATALYSTS

[75] Inventors: Ralph M. Dessau, Edison, N.J.; Ying-Yen P. Tsao, Lahaska, Pa.

[73] Assignee: Mobil Oil Corporation, Fairfax, Va.

[21] Appl. No.: 600,889

[22] Filed: Oct. 22, 1990

[51] Int. Cl.$^5$ .................. B01J 21/06; B01J 29/04
[52] U.S. Cl. ........................ 502/66; 502/60; 502/74
[58] Field of Search ............... 502/66, 71, 60

[56] References Cited

U.S. PATENT DOCUMENTS

| | | | |
|---|---|---|---|
| Re. 29,948 | 3/1979 | Dwyer et al. | 208/110 |
| 3,702,293 | 11/1972 | Hayes et al. | 208/139 |
| 3,702,294 | 11/1972 | Rausch | 208/139 |
| 3,878,131 | 4/1973 | Hayes | 252/466 PT |
| 4,104,320 | 8/1978 | Bernard et al. | 260/673.5 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,465,889 | 8/1984 | Anthony et al. | 502/71 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,563,435 | 1/1986 | Chu et al. | 502/71 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,868,145 | 9/1989 | Dessau et al. | |
| 4,962,075 | 10/1990 | Green et al. | 502/71 |
| 4,990,710 | 2/1991 | Dessau et al. | 585/277 |

FOREIGN PATENT DOCUMENTS

| | | |
|---|---|---|
| 74651 | 1/1976 | European Pat. Off. |
| 0107389 | 4/1984 | European Pat. Off. |
| 2520636 | 1/1983 | France |
| 2033358 | 5/1980 | United Kingdom |
| 2114150 | 8/1983 | United Kingdom |

OTHER PUBLICATIONS

G. Wengui et al "IR Study of Framework Vibrations and Surface Property High Silica Zeolites", Zeolites, Elsevir Science, Amsterdam, 1985, p. 2.

Ione, Journal of Molecular Catalysis, 31, pp. 355-370 (1985).

Ione, "Structure and Reactivity of Modified Zeolites", Elsevir Science (1984), pp. 151-155.

*Primary Examiner*—Carl F. Dees
*Attorney, Agent, or Firm*—Alexander J. McKillop; Charles J. Speciale; Marina V. Schneller

[57] ABSTRACT

The aging properties of Group VIII metal modified non-acidic microporous crystalline materials which in catalysis exhibit high selectivity for dehydrogenation and dehydrocyclization are improved by the incorporation therein of titanium and/or titania.

33 Claims, 1 Drawing Sheet

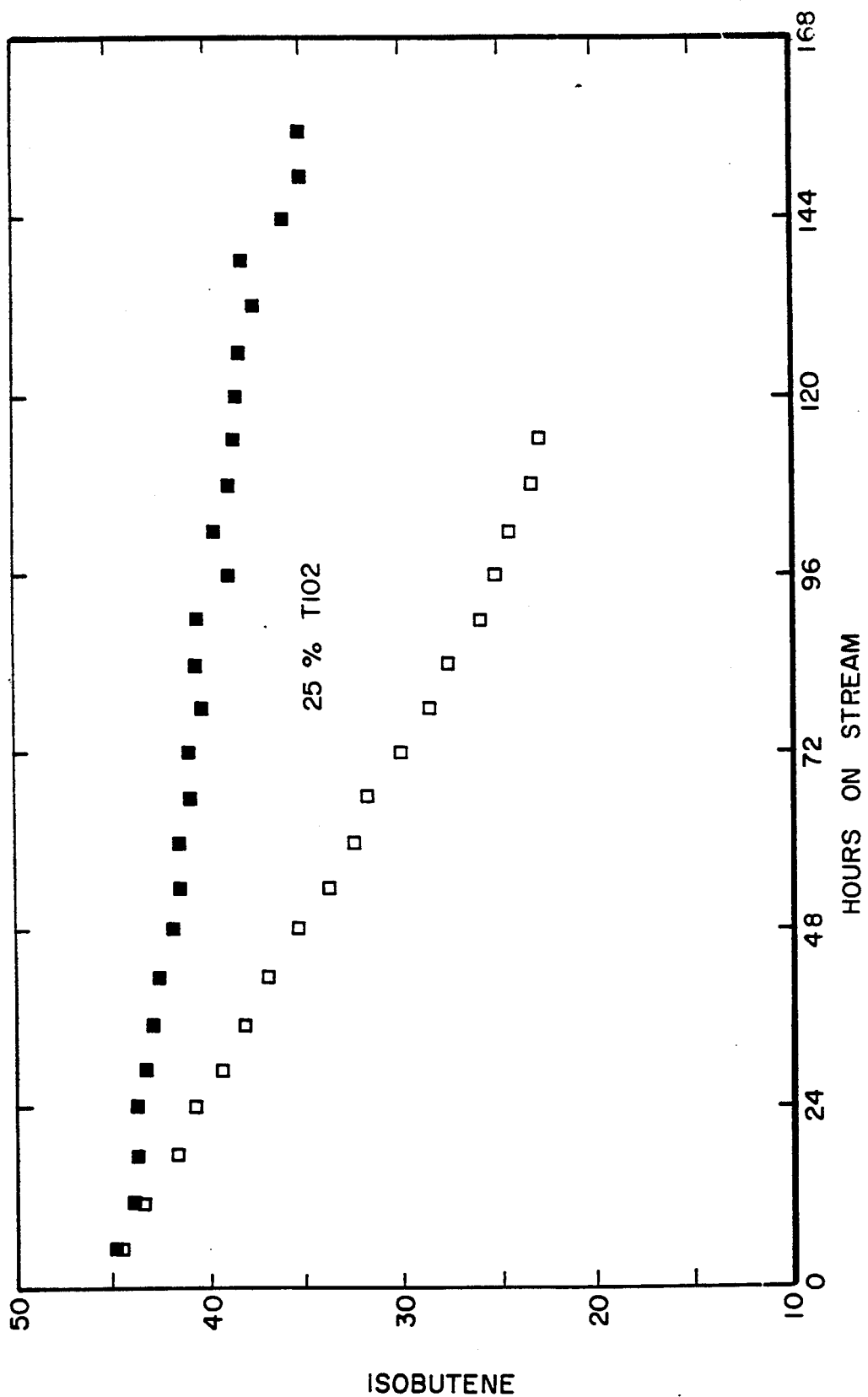

TITANIA CONTAINING DEHYDROGENATION CATALYSTS

FIELD OF THE INVENTION

Non-acidic microporous crystalline materials in combination with platinum group metals, as catalysts, have been found to exhibit high dehydrogenation and dehydrocyclization selectivity under dehydrogenation and dehydrocyclization conditions of paraffins for production of the olefinic analog of the paraffin.

The present invention is directed to maintaining catalyst life of those catalysts by increasing stability and decreasing aging. Accordingly, the invention relates to increasing cycle life in dehydrogenations and dehydrocyclizations, by decreasing catalyst aging, and thereby increasing catalyst stability. In accordance with the invention, those non-acidic microporous crystalline materials are combined with forms of titanium, to decrease catalyst aging during those processes. Moreover, that decrease in catalyst aging can result in increasing cycle life between catalyst regeneration(s).

Various dehydrogenation products are commercially significant. Isobutylene is one such desirable product which is used as a reactant for the production of alkylate, an oligomer of petroleum refinery $C_3$–$C_4$ off gases, which includes high octane gasoline components, and for the production of methyl-t-butyl ether, when isobutylene is reacted with methanol.

The main object of the invention is to provide a dehydrogenation/dehydrocyclization catalyst with improved aging properties and exhibiting high selectivity in cyclical processes.

Accordingly, an object of the process is to produce olefins with high selectivity.

Another object of the invention is to produce isobutylene product with high selectivity. Yet another object of the invention is to produce isobutylene product substantially free or any of the $C_4$ isomers other than isobutylene.

BACKGROUND OF THE INVENTION

The term "crystalline" used to refer to these materials relates to the ordered definite crystalline structure of the material which is unique and thus identifiable by a characteristic X-ray diffraction pattern.

The term "microporous" as it refers to such material relates to pores, or channels, with diameters of less than 20 Angstroms. Examples of these microporous crystalline materials include crystalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOs and SAPOs, have pores of uniform size and channel systems which are uniquely determined by unit structure of the material. The uniform pore size and/or channel systems allow such a material to selectively absorb molecules of certain dimensions and shapes. In the art, microporous material having pores, or channels, of less than 20 Angstroms, can be divided into small, medium and large pore by the diameters of those pores, or channels. The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical. Alternatively, the demarcation between small, medium, and large pore materials can be based on the following sorption properties (measured at room temperature for crystallites having a minimum dimension of 0.1 micron):

1. Small pore: $n$-$C_6$/$i$-$C_6$ sorption ratio greater than approximately 10.
2. Medium pore: $n$-$C_6$/$i$-$C_6$ is less than 10 and $n$-$C_6$/Mesitylene sorption ratio greater than approximately 5.
3. Large pore: $n$-$C_6$/Mesitylene sorption ratio less than approximately 5.

In the art, zeolites are a subclass of crystalline microporous silicates. Zeolites can contain aluminum as well as silicon. In some zeolites, the upper limit of the silicon/aluminum atomic ratio is unbounded. ZSM-5 is one such example wherein the silicon/aluminum atomic ratio is at least 2.5 and up to infinity. By way of illustration, U.S. Pat. No. 3,941,871, reissued as U.S. Pat. No. Re. 29,948, discloses a porous crystalline silicate made from a reaction mixture containing no deliberately added aluminum and exhibiting the X-ray diffraction pattern characteristic of ZSM-5 zeolites; in certain examples tin is deliberately added to the silicate synthesis mixture.

Zeolites can be acidic or non-acidic, depending on the framework aluminum content and on the amount of compensating cations, such as $Na^+$, $K^+$, etc. ALPOs described in U.S. Pat. No. 4,310,440, which is incorporated by reference herein, are neutral. SAPOs described for example in U.S. Pat. No. 4,440,871, which is incorporated by reference herein, can be acidic or non-acidic depending on the ratio of framework Al:P therein and the compensating cation, such as $Na^+$, $K^+$ (other than proton species and other than proton forming species such as $NH^+_4$).

SUMMARY OF THE INVENTION

The invention relates to contacting alkyl containing compounds in the presence of a non-acidic catalyst, under dehydrogenation/dehydrocyclization conditions to produce the alkenyl analog of the alkyl containing compounds and hydrogen, while substantially maintaining the yield during the dehydrogenation/dehydrocyclization cycle conditions. The invention also relates to increasing the time duration of the dehydrogenation/dehydrocyclization cycle, prior to catalyst regeneration. The non-acidic catalyst comprises a platinum group metal, the non-acidic microporous crystalline material, titanium or titania, wherein the amount of titanium and/or titania is effective to decrease the aging of the non-acidic microporous crystalline material, under said conditions of paraffin dehydrogenation and paraffin dehydrocyclization.

In a preferred embodiment, the composition comprises a microporous crystalline material containing tin as a modifier. It has been discovered that these tin containing microporous crystalline materials in non-acidic form combined with a dehydrogenation metal exhibit high selectivity for dehydrogenation and/or dehydrocyclization of paraffins, while exhibiting decreased selectivity for hydrogenolysis (especially methane formation) relative to their tin-free counterparts. Furthermore, these compositions are effective reforming catalysts.

DESCRIPTION OF THE DRAWING

The FIGURE shows the effect of titania on the production of dehydrogenation in a graph of a plot of isobutene (production) vs. days on stream.

DETAILED DESCRIPTION OF THE INVENTION

The non-acidic catalyst comprises a hydrogenation/dehydrogenation metal, the non-acidic microporous crystalline material, titanium or titania, wherein the amount of titanium and/or titania is effective to decrease the aging of the non-acidic microporous crystalline material, under said conditions. As catalysts these non-acidic forms of compositions exhibit extremely high selectivity for paraffin dehydrogenation and/or dehydrocyclization reactions, under conditions effective for paraffin dehydrogenation and/or aromatization.

The amount of hydrogenation/dehydrogenation metal in the catalyst can range from 0.1 to 30 weight percent and preferably 0.01 to 10 weight percent of the crystalline tin containing material. In a preferred embodiment, platinum is the hydrogenation/dehydrogenation metal. However, the hydrogenation/dehydrogenation metal can be any Group VIII metal including those of the platinum group, chromium and vanadium.

The microporous crystalline materials, if acidic as a result of synthesis, can be rendered non-acidic by base exchange to remove acidic functions contained therein. For example, if the microporous crystalline material contains framework aluminum, in the as-synthesized form, the microporous crystalline material can be base exchanged. In this embodiment, base exchange is effected after hydrogenation/dehydrogenation metal incorporation. Base exchange can be with an ionic Group IA or Group IIA metal. The base-exchange can be accomplished by slurring the material in an aqueous solution of suitable Group IA compound such as sodium hydroxide, potassium chloride, cesium hydroxide and the like. The base exchange can be accomplished under selected conditions of reagent concentration, pH, contact time, and the like, so as to eliminate substantially the base-exchangeable acidic content. Such a base-exchanged hydrogenation/dehydrogenation metal containing zeolite is essentially "non-acidic", and exhibits substantially no acid-catalyzed reactivity when employed as a catalyst in hydrocarbon conversions, such as cracking.

In a preferred embodiment the microporous crystalline material is non-acidic, in the as-synthesized form. In a preferred embodiment, the microporous crystalline material contains a modifier selected from the group consisting of tin, indium, thallium and lead. The modifier content of the crystalline microporous materials can range from 0.01 to 20 weight percent. Practically, the modifier content will range from 0.1 to 10 weight percent. Synthesis of these modifier containing microporous crystalline materials are described in U.S. Pat. Nos. 4,886,926, 4,931,416 and 4,868,145 each of which is relied upon and incorporated by reference herein, as well as in allowed application Ser. No. 211,198, filed Jun. 24, 1988, which is relied upon and incorporated by reference herein.

The crystalline microporous materials of the invention are characterized by Si/Al ratios of at least 2. However, the silica:alumina ratio can be up to 1000, or greater. In a preferred embodiment the aluminum content of these materials is less than 0.1 weight percent and more preferably less than 0.02 weight percent.

The crystalline microporous material of the invention can contain other elements including boron, iron, chromium and gallium. The content of these other elements in the crystalline microporous materials can range from 0 to 10 weight percent.

The crystalline materials of the invention, described herein, are crystalline in the sense that they are identifiable as isostructural with zeolites by X-ray powder diffraction pattern.

The crystalline microporous tin containing material has an X-ray diffraction pattern which corresponds to a zeolite, SAPO, ALPO, etc.

In a preferred embodiment the pore size of the microporous crystalline tin containing silicates ranges from about 5 to about 8 Angstroms. Preferably, the silicates exhibit X-ray diffraction patterns of zeolites which are characterized by Constraint Index of 1 to 12.

The method by which Constraint Index is determined is described fully in U.S. Pat. No. 4,016,218, incorporated herein by reference for details of the method. Constraint Index (CI) values for some typical zeolites including some which are suitable as catalysts in the process of this invention are:

| | CI (at test temperature) |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those zeolites which are useful in the process of the present invention. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI value within the range of 5 or less, depending on the temperature employed during the test method within the range of 290° C. to about 538° C., with accompanying conversion between 10% and 60%, the CI may vary within the indicated range of 5 or less. Accordingly, it will be understood to those skilled in the art that the CI as utilized herein, while affording a highly useful means for characterizing the zeolites of interest, is approximately taking into consideration the manner of its determination including the possibility in some instances of compounding variable extremes. However, in all instances, at a temperature within the above-specified range of 290° C. to about 538° C., the CI will have a value for any given zeolite of interest herein of not greater than about 5 and preferably not greater than about 3.

In a preferred embodiment the microporous crystalline material exhibits the structure of ZSM-5, by X-ray diffraction pattern. The X-ray diffraction pattern of ZSM-5 has been described in U.S. Pat. No. 3,702,886 and U.S. Pat. No. Re. 29,948 each of which is incorporated by reference herein.

The compositions comprising hydrogenation/dehydrogenation metal combined with the crystalline microporous materials do not exhibit any appreciable acid activity. These catalysts would meet the criteria of non-acidic catalysts described by Davis and Venuto, J. CATAL. Vol. 15, p.363 (1969). Thus, a non-equilibrium mixture of xylenes are formed from either n-octane or each individual methylheptane isomer, with the octane yielding more o-xylene and 2-methyl-heptane yielding mostly m-xylene, at conversions between 10 and 60%.

When, as in embodiments herein, the crystalline microporous dehydrogenation metal containing material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

In accordance with the invention, the titanium or titania containing compositions exhibit not only the high selectivity for dehydrogenation, but also exhibit excellent aging characteristics, with attendant benefits on cycle life and cycle yields. The titanium, expressed as $TiO_2$, or catalytically inert titania can be present in amounts ranging from 0.1 to 90 weight percent of the catalyst composition. The titanium source may be admixed directly with the microporous crystalline material prior to noble metal incorporation or the titanium source may be admixed with the microporous crystalline material after noble metal incorporation. Introduction of the titanium can be via organic or inorganic titanium compounds in solutions which are impregnated, deposited or exchanged onto the microporous crystalline material. Alternatively, the titanium compound, e.g. the halides, may be vaporized and contacted with the microporous crystalline material, as a gaseous titanium compound. Alternatively, the titanium source may be added directly to the microporous crystalline material synthesis reaction mixture.

Compositions of the invention used in catalysis decrease the hydrogen content of the reactant to produce a product having the same number of carbon atoms as the number of carbon atoms in reactant. By comparison acidic counterparts of those compositions catalyzed also cracking of paraffins, as a major competing side reaction; and, accordingly, the latter compositions exhibit decreased selectivity for the dehydrogenation and dehydrocyclization (aromatization) of paraffins but increased selectivity for $C_1$-$C_5$ paraffin production.

In a preferred embodiment, the non-acidic crystalline microporous tin containing silicates of the invention are treated with $Pt(NH_3)_4Cl_2$ in aqueous solution which has a pH of at least about 7 to incorporate the necessary platinum for catalyst composition formulation.

The non-acidic, crystalline, microporous modifier and dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica, when the materials of the invention are used in dehydrogenation/hydrogenation or dehydrocyclization. The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The compositions of the invention exhibit high selectivity for dehydrogenation and/or dehydrocyclization which is evidenced by the examples.

Catalytic Dehydrogenation and Dehydrocyclization

In accordance with the invention catalytic dehydrogenation comprises contacting an aliphatic, with the catalyst composition of the invention to produce the corresponding unsaturated analog together with $H_2$. The catalytic dehydrogenation exhibits high selectivity with respect to production of said unsaturated analog, with substantially little, if any, selectivity for hydrogenolysis (cracking) and with substantially little, if any, selectivity for isomerization.

In dehydrogenation the feedstocks comprise at least one unsubstituted or substituted straight or branched chain aliphatic compound in which the aliphatic moiety has two to five carbon atoms. In accordance with the invention, dehydrogenation of the aliphatic moiety occurs to yield the unsaturated analog. When the aliphatic moiety is substituted, the substituents can be aryls substituted or unsubstituted. The class of reactants includes alkanes of 2 to 5 carbon atoms, such as ethane, propane, butane, isobutane, pentane and 2 methylbutane. Dehydrogenation of those respective alkane reactants will yield ethylene, propylene, butene, isobutene, pentene and isopentene.

The class of reactants includes olefins of 2 to 5 carbon atoms such as ethylene, butene, isobutene, pentene, and isopentene. Dehydrogenation of ethylene will produce acetylene; dehydrogenation of butene will produce butadiene and dehydrogenation of isopentene will produce isoprene.

The class of reactants employed in the dehydrogenation of the invention includes aromatic substituted aliphatics, aryl substituted aliphatics. Preferably, the aliphatic group of the aryl substituted aliphatic contains less than four carbon atoms and more preferably more than 1 carbon atom. The aryl substituted aliphatic reactants embrace unsubstituted arylaliphatics and alkyl substituted aryl aliphatics and; similarly, each of the alkyls of said alkyl substituted alkylaryls contains preferably less than 4 carbon atoms. By way of illustration reactants such as ethyl benzene, diethylbenzene, ethyl toluene, and cumene are representative of these compounds. On dehydrogenation in accordance with the invention, ethyl benzene will produce styrene; ethyl toluene will produce p-methylstyrene; cumene, iso-propenylbenzene; and diethylbenzene, divinylbenzene.

In accordance with the invention, catalytic dehydrogenation conditions include pressures varying from subatmospheric, to atmospheric to greater than atmospheric. Preferred pressures range from 0.1 atmospheres to atmospheric. However, pressures up to 500 psig can be employed. The dehydrogenation is conducted at elevated temperatures ranging from 400° C. to 700° C. and most preferably from 300° C. to 600° C. Reactor inlet $H_2$/feed ratios are 5 or less; even at reactor inlet ratios of zero (0), there will be a hydrogen partial pressure in the reactor because hydrogen is a bi-product of dehydrogenation. The liquid hourly space velocity of 0.1 to 50, preferably 0.5 to 10.

Under these conditions, the catalytic dehydrogenation of the invention exhibits little if any selectivity for hydrogenolysis or for isomerization. Accordingly, the unsaturated product of the process of the invention can be characterized as substantially free of molecular products of less (fewer number) carbon atoms than the reactants and as substantially free of isomers of the reactant or of isomers of its unsaturated analogs of the reactant.

Dehydrogenation may be conducted in the presence or absence of purposefully added hydrogen and in the presence of diluents inert to conditions of the catalytic dehydrogenation such as nitrogen and methane. In particular, dehydrogenation can be advantageously conducted at low hydrogen pressure.

Dehydrocyclization in accordance with the invention comprises contacting an aliphatic of at least six (6) carbon atoms with the catalytic composition comprising a dehydrogenation/hydrogenation metal which can be any Group VIII metal, preferably platinum.

In accordance with the invention, catalytic dehydrocyclization conditions include pressures varying from subatmospheric, to atmospheric to greater than atmospheric. Preferred pressures range from 0.1 atmospheres to atmospheric. However, pressures up to 500 psig can be employed. The dehydrocyclization is conducted at elevated temperatures ranging from 400° C. to 700° C. and most preferably from 300° C. to 600° C.

Reactor inlet $H_2$/feed ratios are 5 or less; even at reactor inlet ratios of zero (0), there will be a hydrogen partial pressure in the reactor because hydrogen is a bi-product of dehydrogenation and dehydrocyclization. The liquid hourly space velocity of 0.1 to 50, preferably 0.5 to 10.

The feedstock charge(s) to the new process can be those which are feedstocks for reforming, such as straightrun, thermal, or hydrocracker naphtha. Preferably, for high increases in the aromatic content and high octane numbers of the reformate, the charge to the reformer is a naphtha rich in $C_6$ and $C_7$ paraffins; these are generally difficult to reform selectively using conventional catalysts (such as chlorided Pt-alumina). Naphthas can be obtained by separating the charge into two fractions: a light naphtha and a heavy naphtha. Conventionally such separation is by distillation. The boiling range of the light naphtha is from about 80° F. to about 400° F. and the boiling range of the heavy naphtha will be from up to about 650° F. The light naphtha will be rich in $C_6$–$C_{10}$ paraffins, and specifically $C_6$ and $C_7$ paraffins. In accordance with one embodiment when the light naphtha is reformed in accordance with the invention, the heavy naphtha will be processed by conventional reforming. The naphtha fractions may be hydrotreated prior to reforming; but hydrotreating is not necessarily required when using the catalyst in accordance with the invention, as the catalyst described below does not appear to be deactivated by, e.g., sulfur. Initial hydrotreating of a hydrocarbon feed serves to convert sulfur, nitrogen and oxygen derivatives of hydrocarbon to hydrogen sulfide, ammonia, and water while depositing metal contaminant from hydrodecomposition of any organo-metal compounds. Where desired, interstage processing of the effluent from the hydrotreating zone may be effected. Such interstage processing may be undertaken, for example, to provide additional hydrogen, to add or remove heat or to withdraw a portion of the hydrotreated stream for treatment which need not be reformed. Hydrotreating of the heavy naphtha fraction may be essential, prior to reforming in a conventional reforming process. Suitably, the temperature in the hydrotreating catalyst bed will be within the approximate range of 550° F. to 850° F. The feed is conducted through the bed at an overall space velocity between about 0.1 and about 10 and preferably between 0.2 and about 2, with hydrogen initially present in the hydrotreating zone in an amount between about 1000 and 10,000 standard cubic feet per barrel of feed, corresponding to a ratio of between about 2.4 and about 24 moles of hydrogen per mole of hydrocarbon. The catalyst may be any of the known hydrotreating catalysts. These include Group VIB metals such as molybdenum, chromium and tungsten and Group VIII metals include nickel, cobalt, palladium and platinum. These metal components are deposited, in the form of metals or metal oxides, on the indicated supports in amounts generally between about 0.1 and about 20 weight percent. One particularly useful hydrotreating catalyst is a commercial catalyst known as Chevron ICR 106 which is a nickel-tungsten-alumina-silica-titania catalyst.

When dehydrogenation, dehydrocyclization or reforming is undertaken over the catalyst in accordance with the invention, the temperature can range broadly from 800° F. to 1100° F., generally being greater than about 900° F., preferably being 900° F. (482° C.) to 1050° F.; the pressure will be from about 0 psig to 500 psig, preferably from 0 psig to 250 psig; inlet $H_2$/hydrocarbon can be 5 or less, even zero (0) (because of hydrogen production during reforming, there will be a hydrogen partial pressure in the unit); while the LHSV (liquid hourly space velocity) can be 0.1 to 20, preferably 0.1 to 10.

EXAMPLES

Example 1

A non-acidic Pt/Sn-ZSM-5 was made to contain 0.8% Pt, 2.5% Sn, 1.0% Na, and 0.12% Al. Synthesis was in accordance with allowed U.S. Ser. No. 211,198 filed Jun. 24, 1988, which is relied upon and incorporated by reference herein. A portion of this catalyst, 1.5 grams, was mixed with 0.6 g titania (Unity 906, 300 $M^2/g$, 81.8% $TiO_2$) in a mortar and plelleted to 14/30 mesh.

Both catalysts were then evaluated for isobutane dehydrogenation at 4.8 WHSV (on zeolite basis), $H_2/C_4=0.5$, 554° C., and atmospheric pressure. The aging behavior of these two catalysts is shown in the FIGURE.

What is claimed is:

1. A non-acidic catalyst comprising
   an amount of titanium in combination with a non-acidic catalyst comprising
   dehydrogenation/hydrogenation metal and a non-acidic microporous crystalline material,
   wherein the amount of the titanium is effective to reduce the aging of said non-acidic composition, under paraffin dehydrogenation conditions.

2. The catalyst of claim 1, wherein the amount of said dehydrogenation/hydrogenation metal ranges from 0.01 to 20 weight percent.

3. The catalyst of claim 1, wherein the microporous crystalline material contains 0.01 to 20 weight percent indium, tin, thallium or lead.

4. The catalyst of claim 1, wherein the non-acidic catalyst contains a Group IA or Group IIA cation.

5. The catalyst of claim 1, wherein the microporous crystalline material contains an amount of tin ranging from 0.01 to 20 weight percent.

6. The catalyst of claim 1, wherein the material has an X-ray pattern of a zeolite.

7. The catalyst of claim 1, wherein the dehydrogenation/hydrogenation metal is a Group VIII metal.

8. The catalyst of claim 1, wherein the dehydrogenation/hydrogenation metal is platinum.

9. The catalyst composition of claim 8, wherein the platinum is intrazeolitic.

10. The catalyst of claim 8, wherein the microporous crystalline material contains an amount of tin ranging from 0.1 to 20 weight percent.

11. The catalyst of claim 9, wherein the microporous crystalline material contains an amount of tin ranging from 0.1 to 20 weight percent.

12. The catalyst of claim 9, wherein the material exhibits the x-ray diffraction pattern of ZSM-5.

13. The catalyst of claim 1, wherein the amount of said titanium expressed as $TiO_2$ ranges from 0.1 to 90 weight percent of the non-acidic catalyst.

14. The catalyst of claim 5, wherein the amount of said titanium expressed as $TiO_2$ ranges from 0.01 to 20 weight percent of the non-acidic catalyst.

15. The catalyst of claim 13, wherein the dehydrogenation/hydrogenation metal is a Group VIII metal.

16. The catalyst of claim 14, wherein the dehydrogenation/hydrogenation metal is platinum.

17. The catalyst of claim 1, wherein the material is isostructural with zeolite and contains cations of alkali metal or alkali earth metal in excess of the aluminum content of the zeolite.

18. The catalyst of claim 1, wherein the material exhibits the x-ray diffraction pattern of ZSM-5, ZSM-11, ZSM-12, ZSM-22, ZSM-23, ZSM-35, ZSM-48 and ZSM-50.

19. The catalyst of claim 18, wherein the material is a silicate.

20. The catalyst of claim 19, wherein the material contains less than 0.1 weight percent aluminum.

21. The catalyst composition of claim 18, wherein the material contains less than 0.1 weight percent aluminum.

22. The catalyst of claim 20 wherein the amount of said titanium expressed as $TiO_2$ ranges from 0.01 to 20 weight percent of the non-acidic catalyst.

23. The catalyst of claim 21, wherein the amount of said titanium expressed as $TiO_2$ ranges from 0.01 to 20 weight percent of the non-acidic catalyst.

24. The catalyst of claim 19 wherein the crystalline material weight contains a percent of tin which ranges up to 10 weight percent.

25. The catalyst of claim 6, wherein the zeolite is characterized by a constraint index of 1 to 12.

26. A non-acidic catalyst consisting essentially of
   an amount of titanium in combination with a non-acidic composition comprising
   dehydrogenation/hydrogenation metal and a non-acidic microporous crystalline material,
   wherein the amount of the catalytically inert form of titanium is effective to reduce the aging of said non-acidic composition, under paraffin dehydrogenation conditions.

27. A non-acidic catalyst consisting of
   an amount of titanium in combination with a non-acidic composition comprising
   dehydrogenation/hydrogenation metal and a non-acidic microporous crystalline material,
   wherein the amount of titanium is effective to reduce the aging of said non-acidic composition, under paraffin dehydrogenation conditions.

28. The catalyst of claim 27, wherein the microporous crystalline material contains an amount of tin, indium, thallium or lead ranging from 0.01 to 20 weight percent.

29. The catalyst of claim 27, wherein the material has an X-ray pattern of a zeolite selected from the group consisting of ZSM-5, ZSM-11, ZSM-12, ZSM-22, ZSM-23, ZSM-35, ZSM-48 and ZSM-50.

30. The catalyst of claim 27, wherein the dehydrogenation/hydrogenation metal is a Group VIII metal.

31. The catalyst of claim 27, wherein the amount of said titanium expressed as $TiO_2$ ranges from 0.01 to 20 weight percent of the non-acidic catalyst.

32. A non-acidic catalyst comprising
   an amount of a catalytically inert form of titanium in combination with a non-acidic composition comprising
   dehydrogenation/hydrogenation metal and a non-acidic microporous crystalline material, wherein the microporous crystalline material exhibits the X-ray diffraction pattern of a zeolite selected from the group consisting of ZSM-5, ZSM-11, ZSM-12, ZSM-22, ZSM-23, ZSM-35, ZSM-48 and ZSM-50,
   wherein the amount of the catalytically inert form of titanium is effective to reduce the aging of said non-acidic catalyst, under catalytic dehydrogenation conditions.

33. The catalyst of claim 32, wherein the amount of said titanium expressed as $TiO_2$ ranges from 0.01 to 20 weight percent of the non-acidic catalyst.

* * * * *